US008527060B2

(12) United States Patent
Amely-Velez et al.

(10) Patent No.: US 8,527,060 B2
(45) Date of Patent: Sep. 3, 2013

(54) SHIELDING TELEMETRY COMMUNICATIONS BETWEEN ACTIVE IMPLANTABLE MEDICAL DEVICES AND EXTERNAL INSTRUMENTS FROM HIGH POWER ELECTRICAL INTERFERERS

(75) Inventors: Jorge N. Amely-Velez, Simi Valley, CA (US); Armando M. Cappa, Granada Hills, CA (US); J. Terry Benson, Federal Way, WA (US); Robel Borja, Valencia, CA (US); Allan R. Schwartz, Thousand Oaks, CA (US); Anthony Li, Stevenson Ranch, CA (US)

(73) Assignee: Pacesetter, Inc., Sylmar, CA (US)

( * ) Notice: Subject to any disclaimer, the term of this patent is extended or adjusted under 35 U.S.C. 154(b) by 19 days.

(21) Appl. No.: 13/303,715

(22) Filed: Nov. 23, 2011

(65) Prior Publication Data

US 2013/0131759 A1    May 23, 2013

(51) Int. Cl.
*A61N 1/36*    (2006.01)

(52) U.S. Cl.
USPC .......................................................... 607/60

(58) Field of Classification Search
USPC .......................................................... 607/60
See application file for complete search history.

(56) References Cited

U.S. PATENT DOCUMENTS

2012/0326886 A1    12/2012    Herman et al.

*Primary Examiner* — Rex R Holmes (57) ABSTRACT

Disclosed herein is a shield for shielding a telemetry wand from electromagnetical interference capable of interfering with telemetry communications between the telemetry wand and an AIMD in a patient. The telemetry wand may include a first side that is configured to be placed against a patient, a second side generally opposite the first side, a lateral side between the first and second sides, a hole extending between the first and second sides, and a cable extending from the lateral side. The shield may include a shell including a wall that defines a volume and an opening in the shell. The volume may be configured to receive therein the telemetry wand such that the second and lateral sides of the telemetry wand face respective portions of the wall and the first side faces the opening in the shell.

13 Claims, 10 Drawing Sheets

SHIELDING TELEMETRY COMMUNICATIONS BETWEEN ACTIVE IMPLANTABLE MEDICAL DEVICES AND EXTERNAL INSTRUMENTS FROM HIGH POWER ELECTRICAL INTERFERERS

FIELD OF THE INVENTION

Aspects of the present invention relate to medical apparatus and methods. More specifically, the present invention relates to preserving the integrity of telemetry communications between an active implantable medical device and an external instrument.

BACKGROUND OF THE INVENTION

Active implantable medical devices (AIMDs) such as, for example, implantable pulse generators like pacemakers and implantable cardioverter defibrillators (ICDs) are implanted in patients to administer electrotherapy to patient hearts. Once implanted in a patient, an external instrument such as, for example, a pulse generator programmer like the Merlin™ programmer as manufactured by St. Jude Medical, Inc., may need to communicate via telemetry with the AIMD to reprogram parameters, view an intracardiac electrogram (IEGM), and observe performance and interactions of the AIMD with the patient.

High power electromagnetical interferers such as, for example, strong magnetic power generating transformers, cathode ray tubes, compressors, and other machinery, are often abundant in a clinical environment. Such high power interferers emit strong electro-magnetic interference in the frequency band of the telemetry used to communicate between the external programmer and the AIMD. These strong, unwanted signals compete with the communications link between the AIMD and external programmer. As a result, the high power interferers can cause degradation of the telemetry link between the AIMD and the external programmer. At a worst case, the telemetry interference can result in an inability to communicate at all between the programmer and the AIMD. The telemetry interference can also result in missing real time data and also corrupted data, which slows down the data transfer and can also contribute to a loss of the telemetry link.

There is a need in the art for a solution to telemetry interference caused by high power interferers in a clinical environment.

BRIEF SUMMARY OF THE INVENTION

An embodiment of the present disclosure may take the form of an electromagnetic shield between a large interferer and the local magnetic field coupling that exists between a telemetry wand and an AIMD. The shield's shape is designed to sit over the telemetry wand, thereby preventing any interference flux from getting close to the flux path between the telemetry wand and the AIMD. In order to accomplish the shielding effect, the shield may be constructed of a high permeability material, which conducts stray magnetic fields away from the zone of telemetry communication. The shield also features inserts that allow the shield to be placed over various generations of wands. A cap configured to be coupled to the inserts can be provided with or without magnets. The shape of the shell of the shield may be designed to maintain the ergonomic design of the wand assembly so that it can conveniently be moved or held by the hand.

An embodiment of the present disclosure may take the form of a shield for shielding a telemetry wand from electromagnetical interference capable of interfering with telemetry communications between the telemetry wand and an AIMD in a patient. The telemetry wand may include a first side that is configured to be placed against a patient, a second side generally opposite the first side, a lateral side between the first and second sides, a hole extending between the first and second sides, and a cable extending from the lateral side. The shield may include a shell including a wall that defines a volume and an opening in the shell. The volume may be configured to receive therein the telemetry wand such that the second and lateral sides of the telemetry wand face respective portions of the wall and the first side faces the opening in the shell.

An embodiment of the present disclosure may take the form of a shield for shielding a telemetry wand from electromagnetical interference capable of interfering with telemetry communications between the telemetry wand and an AIMD in a patient. The telemetry wand may include a first side that is configured to be placed against a patient, a second side generally opposite the first side, a lateral side between the first and second sides, a hole extending between the first and second sides, and a cable extending from the lateral side. The shield may include a shell and a structure. The shell may include a wall that defines a volume and an opening in the shell. The structure may extend from an inner surface of the shell towards the opening in the shell. When the telemetry wand is received in the volume, the structure extends into the hole of the telemetry wand and engages the telemetry wand in a manner that retains the telemetry wand in the volume.

While multiple embodiments are disclosed, still other embodiments of the present disclosure will become apparent to those skilled in the art from the following detailed description, which shows and describes illustrative embodiments of the disclosure. As will be realized, the invention is capable of modifications in various aspects, all without departing from the spirit and scope of the present disclosure. Accordingly, the drawings and detailed description are to be regarded as illustrative in nature and not restrictive.

DETAILED DESCRIPTION

Implementations of the present disclosure involve a shield 10 configured to receive therein a telemetry wand 15 of an external programmer 20 used to program and monitor an active implantable medical device (AIMD) 25 such as, for example, a pacemaker, ICD or other pulse generator. The shield 10 is configured to preserve telemetry communications between the AIMD 25 and the telemetry wand 15 when in an environment having high power electromagnetical interferers. For example, in one embodiment, the shield 10 acts as an electromagnetic (EMI) shield between a large interferer and the local magnetic field coupling that exists between the telemetry wand 15 and AIMD 25. The shape of the shield 10 is configured to sit over the telemetry wand 15, thereby preventing any interference flux from getting close to the flux path between the telemetry wand and the AIMD 25.

In one embodiment, in order to accomplish the shielding effect, enclosure components of the shield 10 are constructed of a high permeability material, which conducts stray magnetic fields away from the zone of telemetry communication. The shield 10 may employ interchangeable elements that allow the shield 10 to securely couple over various generations of telemetry wands 15 in a manner that allows the shield 10 to protect the telemetry communications of the telemetry wands 15. Some versions of the interchangeable elements of the shield 10 may contain magnets for activating telemetry (e.g., via activating reed switches in early model AIMDs or activating GMR sensors in later model AIMDs. Other versions of the interchangeable elements may be without such magnets as some models of AIMDs may not employ reed switches or GMR sensors to activate the telemetry link.

Figure 1:
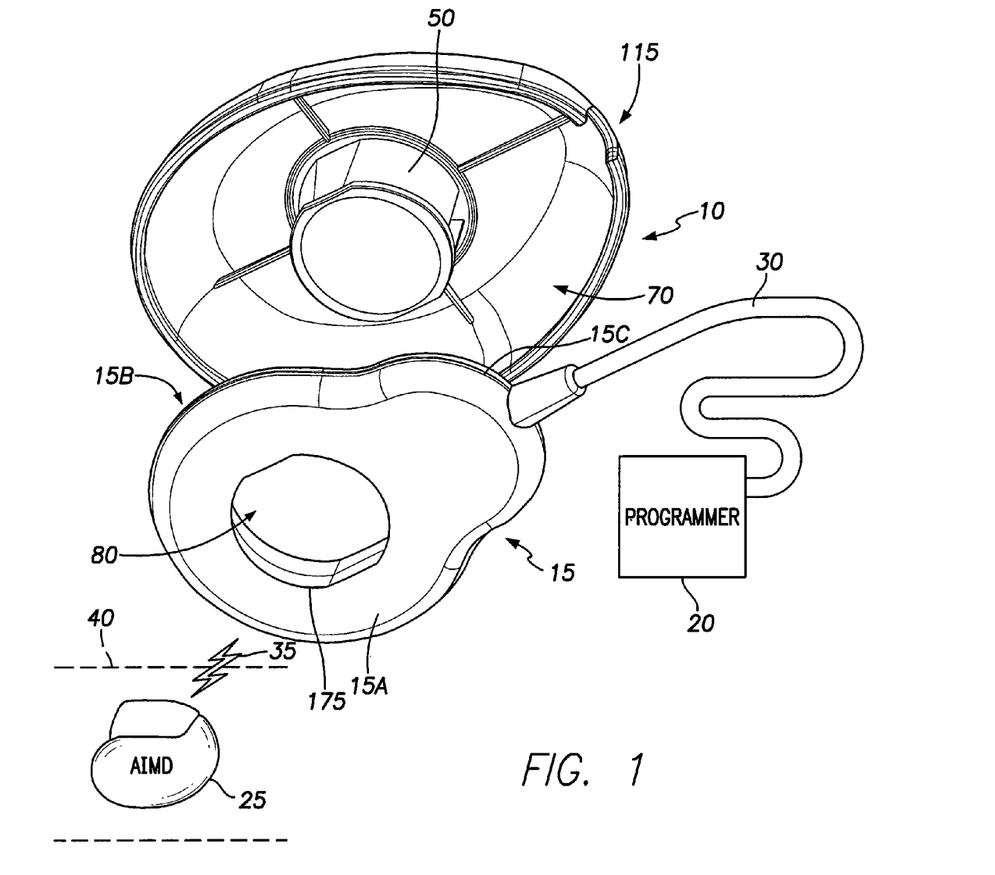
FIG. 1 is an isometric view of a telemetry wand of an AIMD external programmer, the telemetry wand positioned to be received in a shield.
Figure 2:
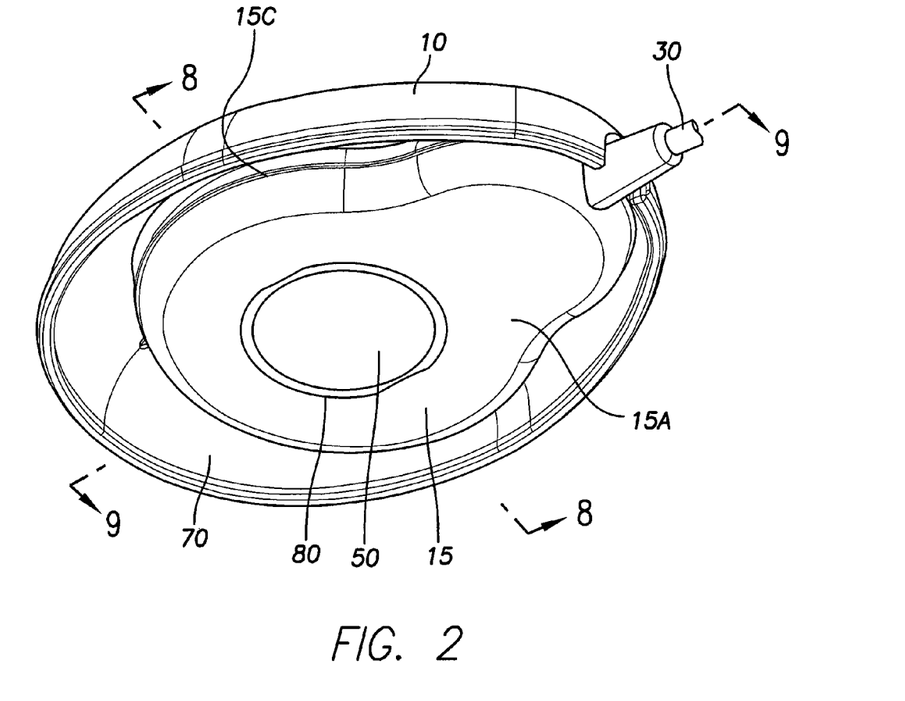
FIG. 2 is generally the same view of the wand and shield as provided in FIG. 1, except the wand has been secured within the volume of the shield.

To begin a detailed discussion regarding the shield 10 disclosed herein, reference is made to FIGS. 1 and 2. FIG. 1 is an isometric view of a telemetry wand 15 of an AIMD external programmer 20, the telemetry wand positioned to be received in a shield 10. FIG. 2 is generally the same view of the telemetry wand 15 and shield 10 as provided in FIG. 1, except the telemetry wand has been secured within the volume of the shield 10.

As illustrated in FIG. 1, the telemetry wand 15 is in electrical communication with the programmer 20 via, for example, an electrically conductive cable 30 that extends between the programmer 20 and the telemetry wand 15. The telemetry wand 15 is capable of wireless communication 35 with an AIMD 25 implanted within a patient 40, the patient 40 being diagrammatically depicted via the dashed lines in FIG. 1. The telemetry wand 15 may include a first side 15A that is configured to be placed against a patient 40, a second side 15B generally opposite the first side 15A, a lateral side 15C between the first side 15A and second side 15B, a hole 80 extending between the first side 15A and second side 15B, and a cable 30 extending from the lateral side 15C. In one embodiment, the surface 15A of the telemetry wand 15 may touch the patient, but the shield enclosing the telemetry wand 15 does not touch the patient when shielding the telemetry wand.

As shown in FIG. 2, the shield 10 is configured to receive therein the telemetry wand 15 such that shield 10 sits over the wand 15, preventing any interference flux from getting close to the flux path between the wand and the AIMD. More specifically, as discussed in more detail below with respect to FIGS. 1-9, the shield 10 includes a shell 45 having a wall 85 that defines a volume 70 and an opening 190 in the shell 45. The volume 70 is configured to receive therein the telemetry wand 15 such that the second side 15B and lateral side 15C of the telemetry wand 15 face respective portions of the wall 85 and the first side 15A faces the opening 190 in the shell 45 (see FIGS. 1 and 8-9).

Figure 3:
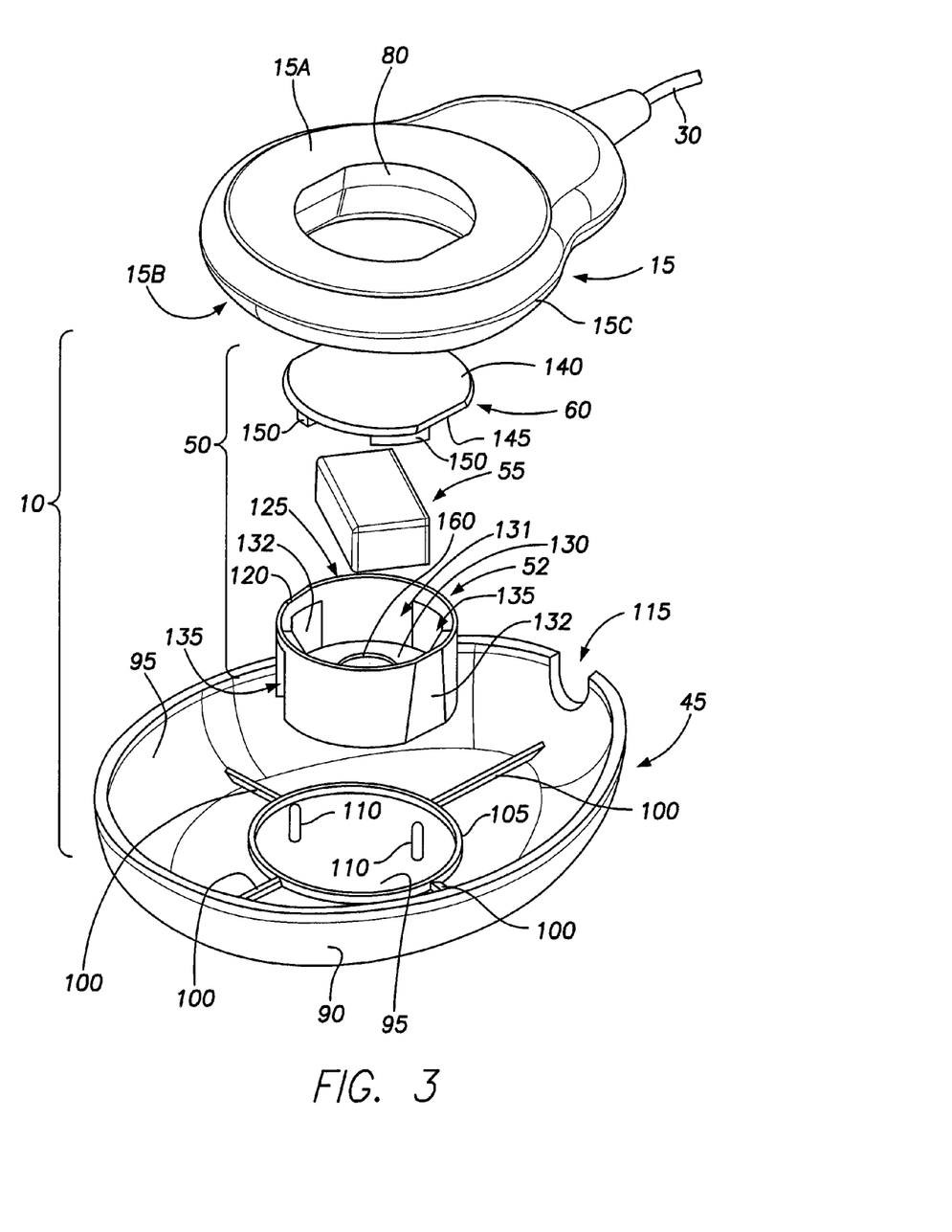
FIG. 3 is an isometric view of the wand and shield, wherein the shield is shown exploded.

FIG. 3 is an isometric view of the telemetry wand aligned with the shield 10 so as to be capable of being received therein, and the shield 10 is shown exploded so as to clearly depict the components of the shield 10. As indicated in FIG. 3, the shield 10 includes a shell 45 and a center island 50. The center island 50 including a magnet housing 52, a magnet 55, and a magnet housing cap 60.

Figure 4:
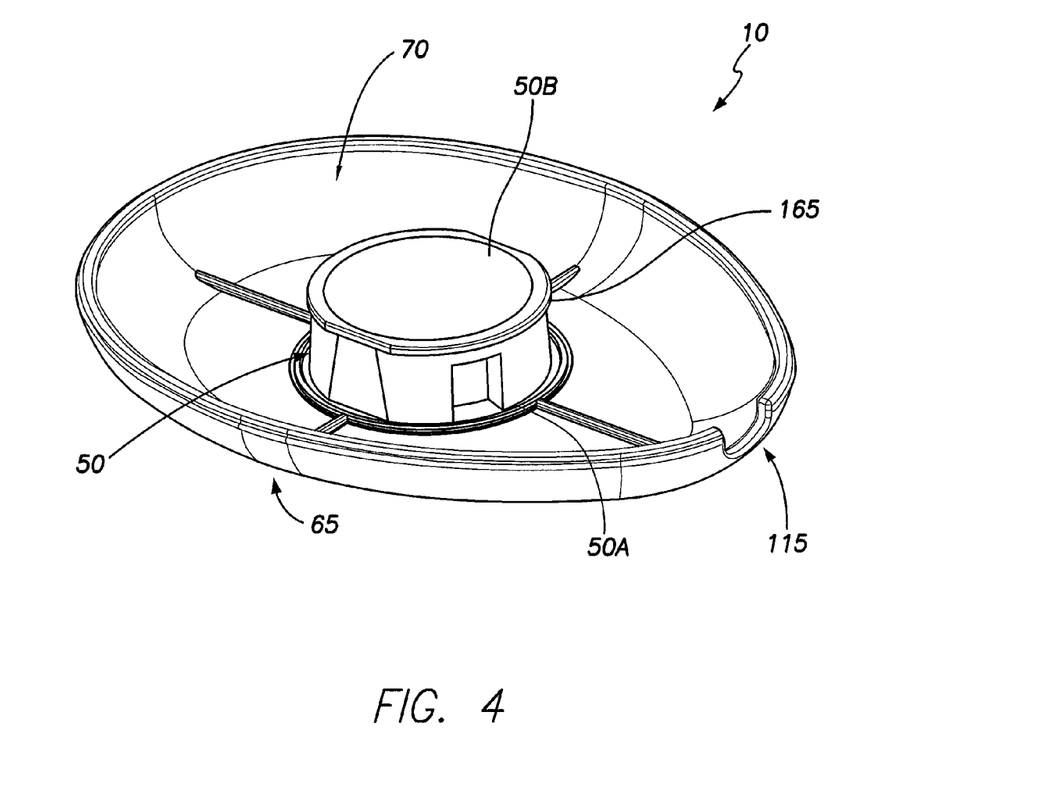
FIGS. 4 and 5 are opposite isometric views of the shield.
Figure 5:
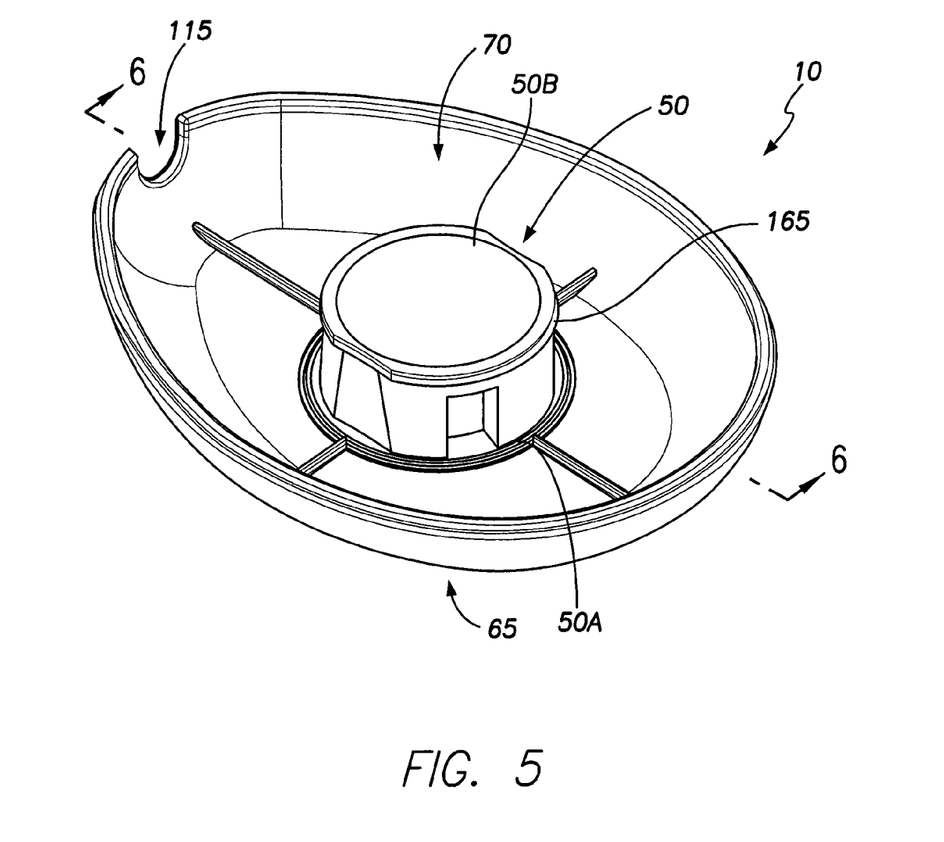

As illustrated in FIGS. 4 and 5, which are opposite isometric views of the shield 10, when the shield 10 is fully assembled, the shield 10 has an outer region 65 and an inner region 70. The outer region 65 of the shield 10 may be generally oval in three dimensions so as to generally resemble a longitudinal half of an egg, thereby providing an ergonomic shape for being gripped by a person's finger and palm surfaces. The inner region 70 may be a volume that is generally oval in three dimensions so as to generally resemble a longitudinal half of an egg, the generally oval volume 70 having an island or center structure 50 projecting outwardly relative to the surrounding surface of the oval volume 70. Thus, as can be understood from FIG. 1, when the shield 10 is properly oriented relative to the telemetry wand 15 so as to allow the telemetry wand 15 to be received in the inner volume 70 of the shield 10, the projecting or raised center structure 50 is aligned with a center hole 80 of the telemetry wand 15. As indicated in FIG. 2, when the telemetry wand 15 is fully received in the inner volume 70 of the shield 10, the center structure 50 is located within, and generally fills, the center hole 80 of the telemetry wand 15.

Figure 6:
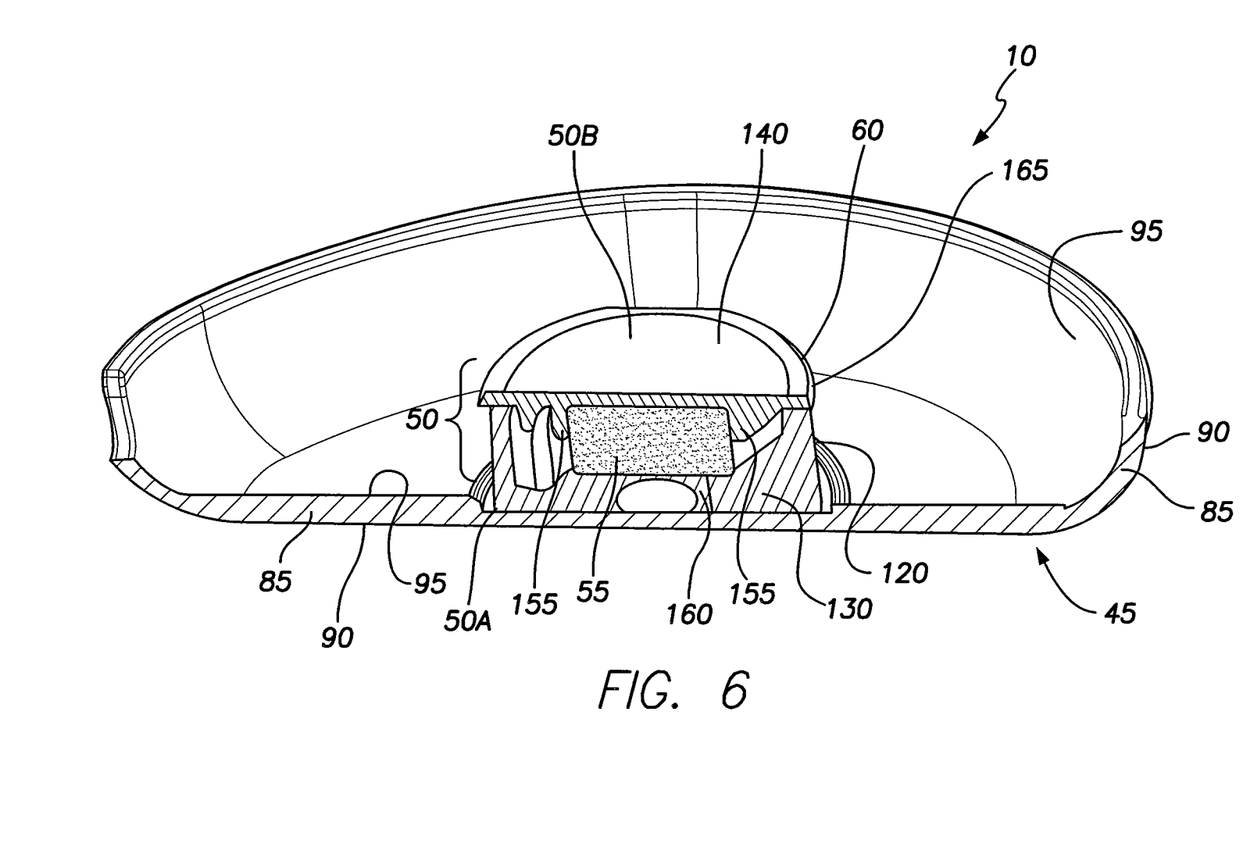
FIG. 6 is a longitudinal isometric cross section of the shield as taken along section line 6-6 in FIG. 5.
Figure 7:
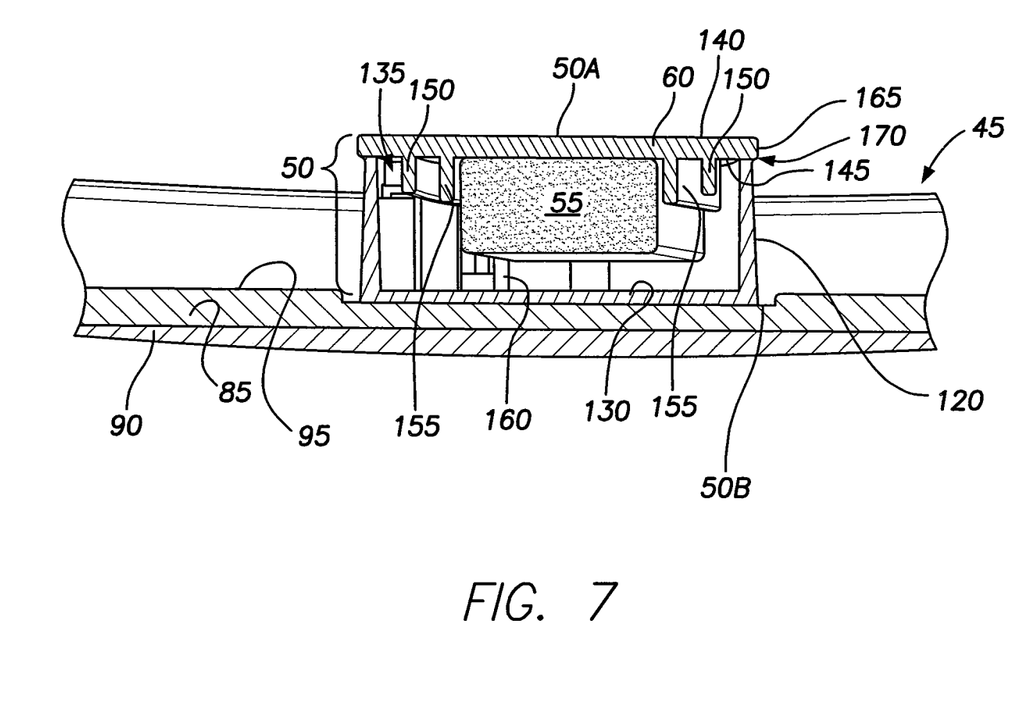
FIG. 7 is generally the same cross section as FIG. 6, except shown more in plan view and as a portion of the overall length of the shield.

FIG. 6 is a longitudinal isometric cross section of the shield 10 as taken along section line 6-6 in FIG. 5. FIG. 7 is generally the same cross section as FIG. 6, except shown more in plan view and as a portion of the overall length of the shield 10. As can be understood from FIGS. 3, 6 and 7, the shell 45 includes a wall 85 that has an outer surface 90 and an inner surface 95. The shell 45 is responsible for the shield 10 having the above-described oval configuration. The outer surface 90 of the shell wall 85 defines the outer region 65 of the shield 10. The inner surface 95 of the shell wall 85 and the projecting center structure 50 define the inner volume 70 of the shield 10.

As illustrated in FIG. 3, the inner surface 95 of the shell wall 85 may include linear ribs 100 lengthwise and sideways from a circular rib 105 generally centered in the inner volume 70 of the shield 10. Protrusions 110 located within the boundary of the circular rib 105 project outward from the inner surface 95 generally perpendicular thereto. A semi-circular notch or opening 115 is defined in the shell wall 85 to allow the telemetry wand cable 30 to exit the shield 10 when the telemetry wand 15 is located within the volume of the shield 10 as shown in FIG. 2. The notch or opening 115 extends from the open area or side 190 of the shell 45.

In one embodiment, shield shell 45 is formed of a highly permeable material such as, for example, stainless steel, nickel, Mu-metal (a nickel-iron plus copper and molybdenum that has a very high magnetic permeability), Permalloy (a nickel-iron magnetic alloy), electric steel (also called lamination steel, silicon electrical steel, silicon steel or transformer steel that is tailored to produce certain magnetic properties), Zamak or Zamac (a family of alloys with a base metal of zinc and alloying elements of aluminum, magnesium and copper) aluminum, zinc, and 1018 stainless steel. Zinc and aluminum may be considered low permeability materials for some applications. However, zinc and aluminum may work in some cases because the source of noise in a hospital is often mostly electrical in nature.

As a result of the material and its enclosing configuration, any flux lines from an outside source get caught up in the shell 45 and do not interfere with the wand. More specifically, the flux lines get rerouted over the shell 45, out the shell edge, back to source and away from the circuits in the wand 15. The shield shell can be manufactured via a variety of methods, including machining, casting or forming.

As can be understood from FIGS. 3, 6 and 7, the center island or structure 50 includes a magnet housing 52, a magnet 55, and a magnet housing cap 60. The magnet housing 52 may be generally cylindrical with a generally cylindrical sidewall 120, an open end 125 and a closed end 130, a volume 131 defined within the boundaries provided by the sidewall 120, open end 125 and closed end 130.

Figure 8:
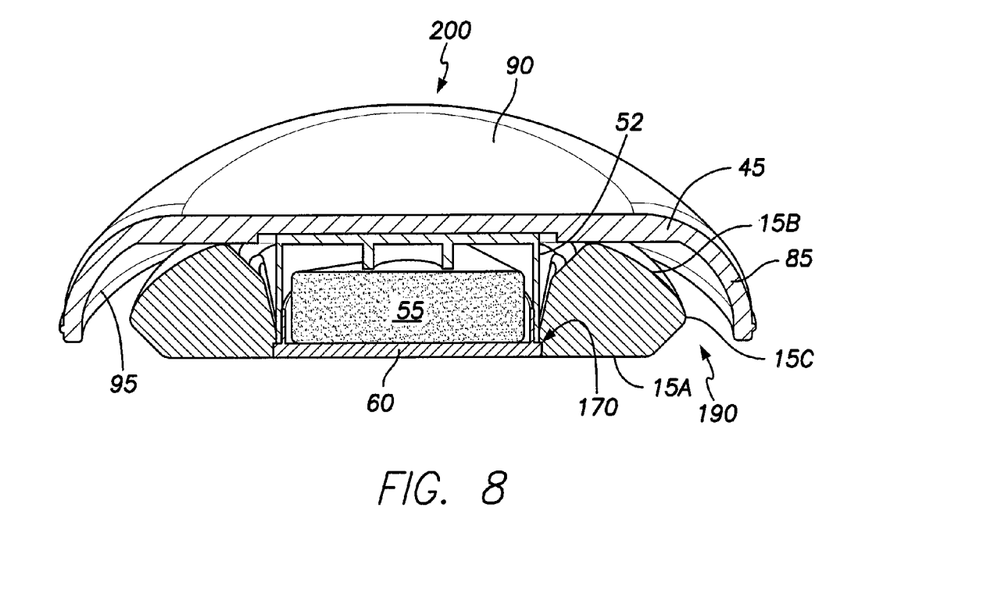
FIGS. 8 and 9 are, respectively, transverse and longitudinal cross sectional elevations of the shield and wand coupled together as respectively taken along section lines 8-8 and 9-9 in FIG. 2.
Figure 9:
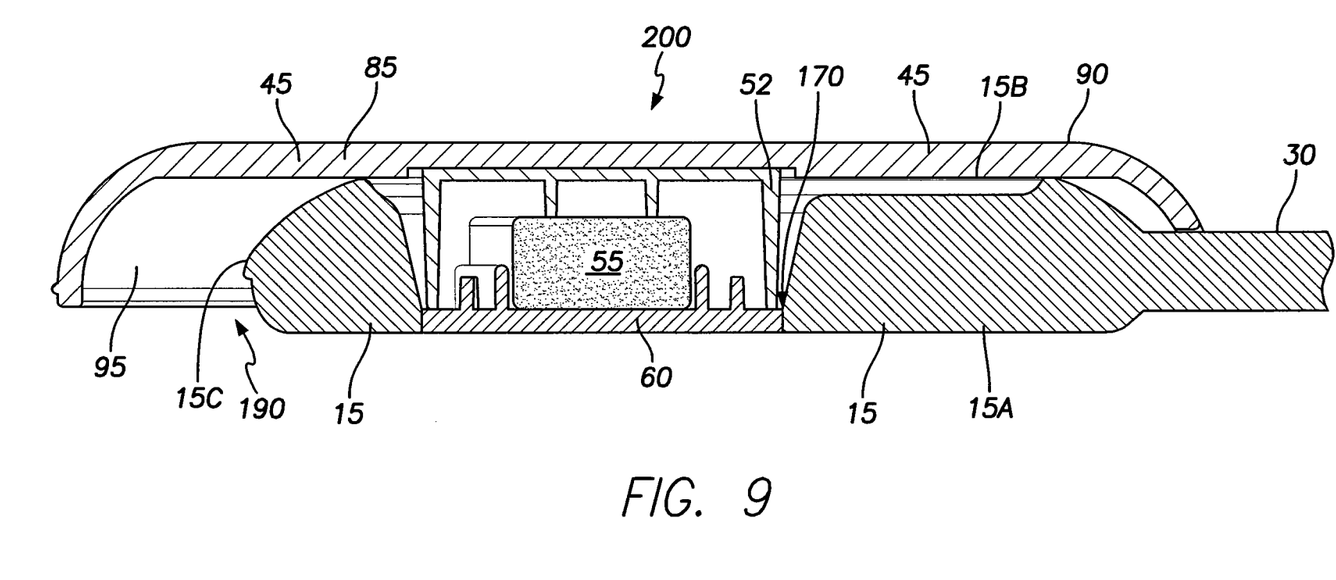

As can be understood from FIGS. 4-7, the center structure 50 extends towards the opening 190 of the shell 45 from an inner surface 95 of the shell 45. The structure may be generally centered in volume 70 of the shell 45. As described in greater detail below, the structure 50 is configured to be received in the hole 80 of the telemetry wand 15 when the telemetry wand 15 is received in the volume 70, as shown in FIGS. 2, 8 and 9. The structure 50 is configured to engage the telemetry wand 15 so as to retain the telemetry wand 15 within the volume 70. The structure 50 includes an inner end 50A that is coupled to the inner surface 95 of the shell 45 and an outer end 50B that is near the opening 190.

The magnet housing 52 may be formed of a polymer or metal material. Engagement features 132, for example, in the form of female openings, are defined in the cylindrical sidewall 120. The engagement features 132 are configured to receive therein a respective protrusion 110 to couple the magnet housing 52 to the inner surface 95 of the shell wall 85. The mechanical coupling arrangement between a protrusion 110 and its respective engagement feature 132 may be via an interference fit, fastener arrangement (e.g., screws interacting between the protrusion 110 and engagement feature 132), adhesive, weld, or any other mechanical coupling arrangement.

As can be understood from FIG. 3, slot and lip arrangements 135 are defined in the cylindrical sidewall 120. The magnet housing cap 60 includes an outer surface 140, an inner surface 145 and tabs 150 that project outwardly from the inner surface 145 of the cap 60. Each tab 150 is configured such that when received in a respective slot and lip arrangement 135, the tab 150 and respective slot and lip arrangement 135 form a bayonet lug arrangement. Thus, with the tabs 150 of the cap 60 received in the respective slot and lip arrangements 135 of the cylindrical magnet housing 52, rotating the cap 60 is a first direction locks the tabs in the slot and lip arrangements, locking the cap 60 to the magnet housing 52. Rotating the cap in a second direction opposite the first direction unlocks the tabs in the slot and lip arrangements, unlocking the cap 60 from the magnet housing 52. The cap 60 may be formed plastic or non-ferromagnetic materials such as, for example, titanium.

As illustrated in FIGS. 6 and 7, some versions of the magnet housing cap 60 will have a magnet 55 secured to the inside surface 145 of the cap 60. For example, planar members 155 may project generally perpendicularly from the cap inner surface 145. The planar sides of the magnet 55 may create an interference fit against the cap planar members 155, or the magnet 55 may be secured to the cap planar members 155 via other arrangements such as, for example, an adhesive. A circular ridge 160 projecting into the volume of the magnet housing 45 from the inner surface of the close end 130 sandwiches the magnet 55 against the inner cap surface 145.

As can be understood from FIGS. 4-7, the diameter of the cap 60 exceeds the diameter of the magnet housing 52 when the cap is coupled to the magnet housing. As a result, the extreme outer circumference 165 of the cap 60 forms a lip 170 (shown in FIG. 7) relative to the outer surface of the sidewall 120 of the magnet housing 52. Thus, as can be understood from FIGS. 8 and 9, which are, respectively, transverse and longitudinal cross sectional elevations of the shield 10 and wand 15 coupled together as respectively taken along section lines 8-8 and 9-9 in FIG. 2, the lip 170 forms an interference fit with the circumferential edge 175 (shown in FIG. 1) of the wand hole 80, thereby acting to secure the wand 15 within the volume 70 of the shield 10. Thus, it can be said that the center structure 50 includes a lip 145 at the outer end 50B of the center structure, and the lip 145 is configured to engage a portion of the telemetry wand 15 at or near hole 80 in retaining the telemetry wand 15 within the volume 70.

Figure 10:
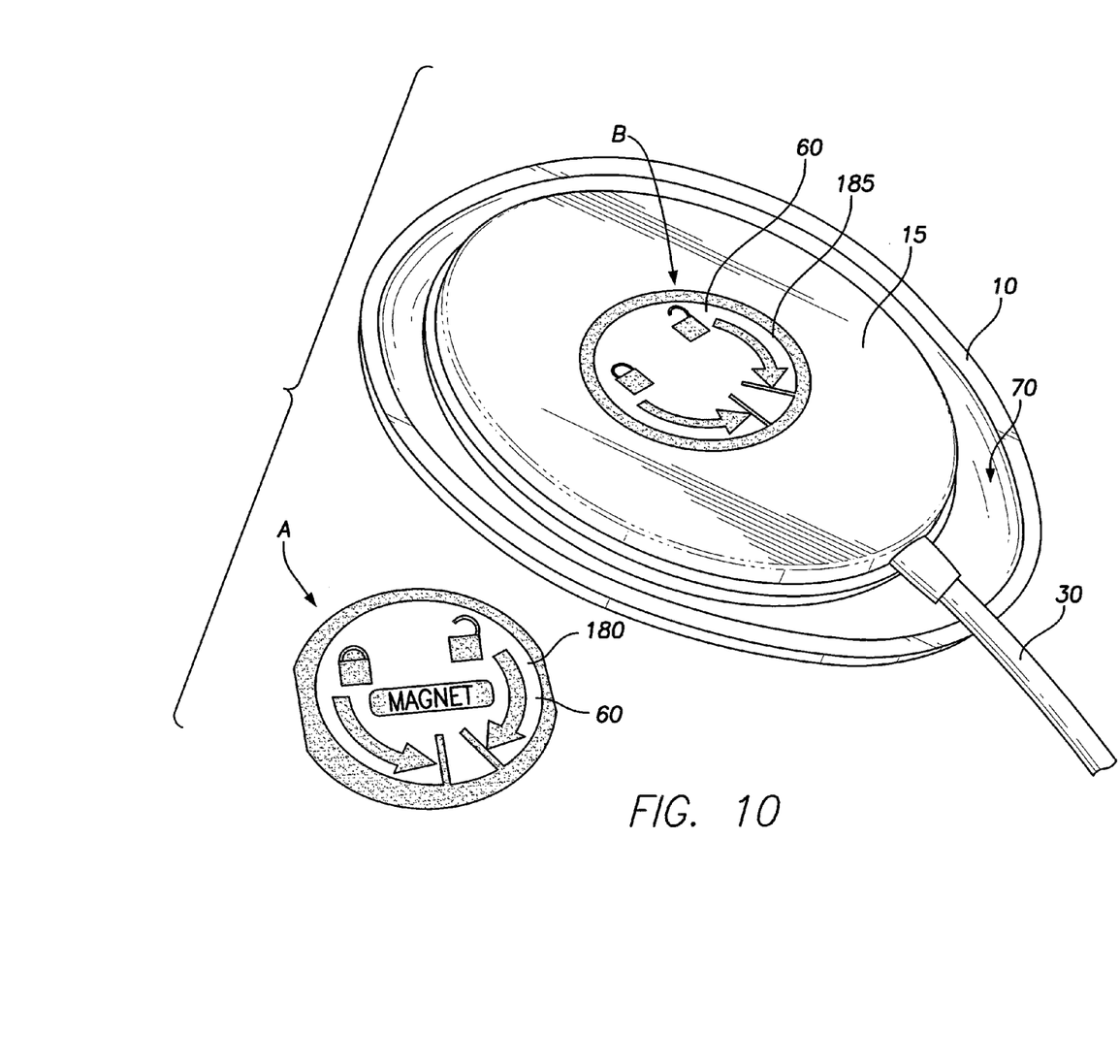
FIG. 10 is an isometric view of the wand received in the shell volume and coupled to the shield via the cap.

As indicated in FIG. 10, which is an isometric view of the wand 15 received in the shell volume 70 and coupled to the shield 10 via the cap 60, the shield 10 may have two caps 60. For example, one cap 60 may be configured as shown in FIGS. 6 and 7 to have a magnet 55 attached to the inside of the cap 60. Such a magnet equipped cap 60 is indicated by arrow A in FIG. 10 and may have a label 180 indicating that the cap is equipped with a magnet. The other cap 60, which is indicated by arrow B in FIG. 10, may be configured similar to the cap 60 depicted in FIGS. 6 and 7, except such a cap may be without a magnet 55 and may have a label 185 indicating that the cap is without a magnet. Thus, the shield 10 may have both a magnet equipped cap 60, as shown at A, and a magnet free cap 60, as shown at B. The two types of caps can be swapped out relative to the rest of the shield 10 depending on whether or not the AIMD 25 the wand 15 will be communicating with requires a magnet in close proximity to activate the telemetry link in the AIMD 25.

In some embodiments, there may be a single cap 60 and the cap 60 and magnet 55 are configured such that the magnet 55 is removed from, or attached to, the cap 60 as needed. Thus, the cap 60 can be removed and reattached to the rest of the center structure 50 in order to allow for the removal or attachment of the telemetry wand 15 to the shield 10, and the magnet 55 can be removed from or attached to the cap 60 as needed. The magnet 55 can be removably attached to the cap 60 by an interference fit, a hook-and-loop material arrangement, a magnetic arrangement, or other mechanical methods.

As can be understood from FIGS. 8 and 9, the volume 70 of the shield 10 may be configured to receive therein the telemetry wand 15 such that the second side 15B and lateral side 15C of the telemetry wand 15 face respective portions of the inner surface 95 of the wall 85 and the first side 15A faces the opening 190 in the shell 45. Each portion of the second side 15B and each portion of the lateral side 15C may be immediately adjacent a respective portion of the inner surface 95 of the wall 85 of the shell 45. For example, depending on the embodiment, the shield shell 45 fits over the wand 15 a specific distance, such as, for example, between approximately 21 mm and approximately 27 mm between an outer surface of the wand and a shield inner surface 95 to permit flux emanating from the wand to go up wand opening 80 and down towards the coils inside the AIMD 25. For example, as can be understood from FIGS. 8 and 9, in one embodiment, each portion of the second side 15B is offset from the respective portion of the inner surface 95 of the wall 85 of the shell 45 by between approximately 2 mm and approximately 7 mm. In one embodiment, each portion of the lateral side 15C is offset from the respective portion of inner surface 95 of the wall 85 of the shell 45 by between approximately 7 mm and approximately 20 mm.

In use, when the telemetry wand 15 is secured within the volume 70 of the shield 10, the shield open side 190 (see FIGS. 8 and 9) is placed against the patient, the shield closed side 200 (see FIGS. 8 and 9) facing away from the patient. The medical professional grasps the shell outer surface 90 and moves the shield open side 190 against the patient until a desirable communication signal is established between the telemetry wand 15 and AIMD 25. As can be understood from FIGS. 1, 8 and 9, the shield 10 encloses the telemetry wand 15 completely except on the shield open side 190 and a small space between the patient surface and the edge of the shield such that the shield does not actually touch the patient.

To secure the telemetry wand 15 in the volume 70 of the shell 45, the cap 60 is removed from the outer end of the center structure 50. The telemetry wand 15 is then oriented relative to the shield 10 such that the non-patient-facing side 15B of the telemetry wand 15 faces the volume 70, the hole 80 is aligned with the center structure 50, and the cable 30 is aligned with the notch 115. With the telemetry wand 15 so oriented, the telemetry wand 15 is then moved into the volume 70 of the shield 10 such that the center structure 50 extends into the hole 80 and the cable 30 is received in the notch 115. The cap 60 is then secured to the rest of the center structure 50 so the lip 170 of the center structure 50 acts against the telemetry wand 15 in the vicinity of the hole 80 to retain the telemetry wand 15 in the volume 70 of the shield 10.

In one embodiment, to secure the telemetry wand in the volume of the shell, the telemetry wand and shield can be oriented as described above, but the cap can remain on the outer end of the center structure. Instead of having to remove the cap from the center structure, the shield can simply be pushed down over the telemetry wand such that the center structure is received in the hole of the telemetry wand and the lip 170 of the cap 60 simply passes through the hole of the telemetry wand to form an interference fit between the lip and hole of the telemetry wand.

In summary, in one embodiment, the shield 10 is configured to minimize the effect of a high power electromagnetical interferer on the telemetry communications between an AIMD in a patient and a telemetry wand 15 of an external programmer 20. Thus, in a clinical environment populated by high power electromagnetical interferers, the shield 10 acts as a barrier between the interferer and the sensitive elements of the telemetry system, permitting normal telemetry to be established and maintained between the telemetry wand 15 positioned within the shield 10 and the AIMD in the patient. In some embodiments, the presence of the shield may cut down on the amplitude of telemetry signals (i.e., the signals that are desired to be preserved), but the telemetry system has enough dynamic range to handle slightly reduced signal levels. The interchangeable caps 60 may be swapped out as necessary to provide a magnet 30 in the shield 10 for actuating reeds switches or GMRs in AIMDs equipped with such switches. The lip 170 formed by the diameter difference between the cap 60 and the rest of the center structure 50 works to maintain the telemetry wand 15 within the volume 70 of the shield 10.

The foregoing merely illustrates the principles of the invention. Various modifications and alterations to the described embodiments will be apparent to those skilled in the art in view of the teachings herein. It will thus be appreciated that those skilled in the art will be able to devise numerous systems, arrangements and methods which, although not explicitly shown or described herein, embody the principles of the invention and are thus within the spirit and scope of the present invention. From the above description and drawings, it will be understood by those of ordinary skill in the art that the particular embodiments shown and described are for purposes of illustrations only and are not intended to limit the scope of the present invention. References to details of particular embodiments are not intended to limit the scope of the invention.

What is claimed is:

1. A shield for shielding a telemetry wand from electromagnetic interference capable of interfering with telemetry communications between the telemetry wand and an AIMD in a patient, the telemetry wand comprising a first side that is configured to be placed against a patient, a second side generally opposite the first side, a lateral side between the first and second sides, a hole extending between the first and second sides, and a cable extending from the lateral side, the shield comprising:
    a shell having a wall that defines a volume and an opening in the shell, the volume configured to receive therein the telemetry wand such that the second and lateral sides of the telemetry wand face respective portions of the wall and the first side faces the opening in the shell;
    wherein the shell comprises a highly magnetically permeable material.

2. The shield of claim 1, wherein, in the volume being configured to receive therein the telemetry wand such that the second and lateral sides of the telemetry wand face respective portions of the wall and the first side faces the opening in the shell, each portion of the second side and each portion of the lateral side are immediately adjacent a respective portion of the wall of the shell.

3. The shield of claim 2, wherein each portion of the second side is offset from the respective portion of the wall of the shell by between approximately 2 mm and approximately 7 mm.

4. The shield of claim 2, wherein each portion of the lateral side is offset from the respective portion of the wall of the shell by between approximately 7 mm and approximately 20 mm.

5. The shield of claim 1, wherein the shell includes a notch that extends into the wall from the opening, the notch being configured to allow the cable to pass from the volume to outside the shell.

6. The shield of claim 1, wherein the highly magnetically permeable material is formed of at least one of the following: stainless steel, nickel, aluminum, zinc, Mu-metal, Permalloy, electric steel, Zamak or Zamac.

7. A shield for shielding a telemetry wand from electromagnetic interference capable of interfering with telemetry communications between the telemetry wand and an AIMD in a patient, the telemetry wand comprising a first side that is configured to be placed against a patient, a second side generally opposite the first side, a lateral side between the first and second sides, a hole extending between the first and second sides, and a cable extending from the lateral side, the shield comprising:
    a shell having a wall that defines a volume and an opening in the shell, the volume configured to receive therein the telemetry wand such that the second and lateral sides of the telemetry wand face respective portions of the wall and the first side faces the opening in the shell; and
    a structure that extends towards the opening from an inner surface of the shell, the structure configured to be received in the hole of the telemetry wand when the telemetry wand is received in the volume, and wherein the structure is configured to engage the telemetry wand so as to retain the telemetry wand within the volume;
    wherein the structure comprises an inner end that is coupled to the inner surface of the shell and an outer end that is near the opening;
    wherein the structure further comprises a lip at the outer end, the lip engaging a portion of the telemetry wand at or near the hole in retaining the telemetry wand within the volume; and wherein the structure further comprises a first cap that is removably coupled to the outer end, a diameter difference between the first cap and the rest of the structure defining the lip.

8. The shield of claim 7, wherein the structure further comprises a second cap that can be exchanged for the first cap, the first cap including a magnetic body and the second cap not including a magnetic body.

9. The shield of claim 7, wherein the first cap comprises a magnetic body that can be removed from, or coupled to, the first cap as needed.

10. The shield of claim 7, wherein the structure is generally centered in the volume of the shell.

11. A shield for shielding a telemetry wand from electromagnetical interference capable of interfering with telemetry communications between the telemetry wand and an AIMD in a patient, the telemetry wand comprising a first side that is configured to be placed against a patient, a second side generally opposite the first side, a lateral side between the first and second sides, a hole extending between the first and second sides, and a cable extending from the lateral side, the shield comprising:
   a shell having a wall that defines a volume and an opening in the shell; and
   a structure extending from an inner surface of the shell towards the opening in the shell:
   wherein, when the telemetry wand is received in the volume, the structure extends into the hole of the telemetry wand and engages the telemetry wand in a manner that retains the telemetry wand in the volume;
   wherein the structure comprises a lip that engages a portion of the telemetry wand at or near the hole in retaining the telemetry wand within the volume;
   wherein the structure includes an outer end near the opening in the shell, and the lip is located at the outer end; and
   wherein the structure further comprises a cap that is removably coupled to the outer end, a diameter difference between the cap and the rest of the structure defining the lip.

12. The shield of claim 11, wherein the volume is configured to receive therein the telemetry wand such that the second and lateral sides of the telemetry wand face respective portions of the wall and the first side faces the opening in the shell.

13. The shield of claim 11, wherein the cap includes a magnet.

* * * * *